US006730750B2

(12) United States Patent
Eaton et al.

(10) Patent No.: US 6,730,750 B2
(45) Date of Patent: May 4, 2004

(54) METHODS FOR FORMING AMORPHOUS ULTRA-HIGH MOLECULAR WEIGHT POLYOLEFINS FOR USE AS DRAG REDUCING AGENTS

(75) Inventors: Gerald B. Eaton, Houston, TX (US); Michael J. Monahan, Katy, TX (US); Alan K. Ebert, Houston, TX (US); Robert J. Tipton, Tulsa, OK (US); Eduardo Baralt, Kingwood, TX (US)

(73) Assignee: Energy & Environmental International, L.C., Brookshire, TX (US)

( * ) Notice: Subject to any disclaimer, the term of this patent is extended or adjusted under 35 U.S.C. 154(b) by 3 days.

(21) Appl. No.: 10/047,763

(22) Filed: Jan. 15, 2002

(65) Prior Publication Data

US 2002/0173600 A1 Nov. 21, 2002

Related U.S. Application Data

(60) Provisional application No. 60/261,767, filed on Jan. 16, 2001.

(51) Int. Cl.$^7$ .............................. C08F 2/02; C08F 4/642
(52) U.S. Cl. ............................. 526/90; 526/75; 526/76; 526/159; 508/591
(58) Field of Search .............................. 526/75, 76, 90, 526/159; 508/591

(56) References Cited

U.S. PATENT DOCUMENTS

| 3,542,044 A | 11/1970 | Hanson et al. |
| 3,645,822 A | 2/1972 | Widiger et al. |
| 3,669,948 A | 6/1972 | Konotsune et al. |
| 3,692,676 A | 9/1972 | Cutler et al. |
| 3,730,275 A | 5/1973 | McClaflin et al. |
| 3,736,288 A | 5/1973 | Stratta et al. |
| 3,767,561 A | 10/1973 | Rossi et al. |
| 3,791,913 A | 2/1974 | Ver Strate et al. |
| 3,843,589 A | 10/1974 | Wartman |
| 3,857,795 A | 12/1974 | Van Der Bend et al. |
| 3,884,252 A | 5/1975 | Kruka |
| 3,944,529 A | 3/1976 | Creemers |
| 3,951,935 A | 4/1976 | Engelmann |
| 4,057,680 A | 11/1977 | Yamazaki et al. |
| 4,142,991 A | 3/1979 | Arzoumanidis et al. |
| 4,147,677 A | 4/1979 | Lundberg et al. |
| 4,190,069 A | 2/1980 | Krantz |
| 4,212,312 A | 7/1980 | Titus |
| 4,262,104 A | 4/1981 | Wristers |
| 4,263,926 A | 4/1981 | Drake et al. |
| 4,267,292 A | 5/1981 | Benton et al. |
| 4,282,114 A | 8/1981 | Ito et al. |
| 4,289,679 A | 9/1981 | Mack |
| 4,294,947 A | 10/1981 | Doerk et al. |
| 4,329,253 A | 5/1982 | Goodall et al. |
| 4,333,488 A | 6/1982 | McClaflin |
| 4,335,964 A | 6/1982 | Drake et al. |
| 4,340,076 A | 7/1982 | Weitzen |
| 4,358,572 A | 11/1982 | Mack et al. |
| 4,371,455 A | 2/1983 | Mack et al. |

(List continued on next page.)

FOREIGN PATENT DOCUMENTS

| CA | 901727 | 5/1972 |
| DE | 19612226 A | 10/1996 |
| EP | 0005215 A | 11/1979 |
| EP | 0108156 A | 5/1984 |
| EP | 0196350 A1 | 8/1986 |
| EP | 0196350 B1 | 11/1989 |
| EP | 0535230 A | 4/1993 |
| EP | 0292797 A | 11/1998 |
| GB | 2074175 A | 10/1981 |
| GB | 2093466 | 9/1982 |
| JP | 2-124904 | 5/1990 |
| WO | WO 95/00563 | 1/1995 |

OTHER PUBLICATIONS

English Language Abstract of Japanese patent application entitled "Preparation of Ethylene–Alpha–Olefin Copolymer," dated May 14, 1990, pub #02124904.

Miscellaneous Patent Summary, pp. 1–118.

Miscellaneous Patent Search, pp. 1–77, dated Aug. 9, 2001.

Miscellaneous Patent Search, pp. 1–204, dated Aug. 13, 2001.

John Boor, Jr., Ziegler–Natta Catalysts and Polymerizations, 1979, Chapter 18: Kinetics, pp. 464–511, Academic Press, New York, USA.

Tad W. Taylor, et al., Physiochemical Kinetics of Liquid Phase Propylene Polymerization, pp. 191–223, Eleventh Midland Macromolecular Meeting, Aug. 17–21, 1981, MMI Press, Midland, MI, USA.

B.M. Grieveson, Kinetics of the Polymerization of Ethylene with a Ziegler–Natta Catalyst, 1965, Die Makromolekulare Chemie, vol. 84, pp. 93–107.

Lutz Wohlfarth, Alternating Copolymerization of Butadiene and Propene with the VO9ONeo)2CI/AI(iso–Bu)3 System 2: Influence of Electron Donors at a Polymerization Temperature of –45 C, 1991, Paste and Kautschuk, vol. 38, No. 9, pp. 297–299 (translation pp. 1–7).

* cited by examiner

Primary Examiner—Roberto Rabago
(74) Attorney, Agent, or Firm—Andrews Kurth LLP; Anthony F. Matheny

(57) ABSTRACT

The present invention is directed to improved drag reducing agents and methods of forming improved drag reducing agents comprising the steps of isomerizing olefin monomers to form isomerized olefin monomers, polymerizing the isomerized olefin monomers in the presence of at least one catalyst to form a polyolefin drag reducing agent having unexpectedly superior drag reduction properties when combined with liquid hydrocarbons, such as viscous crude oil. Therefore, the drag reducing agents of the present invention may be introduced into conduits, such as pipelines, to increase the flow of the hydrocarbons through the conduit.

19 Claims, 2 Drawing Sheets

U.S. PATENT DOCUMENTS

| | | | |
|---|---|---|---|
| 4,384,089 A | 5/1983 | Dehm | |
| 4,393,182 A | 7/1983 | Goodall et al. | |
| 4,395,358 A | 7/1983 | Wristers | |
| 4,403,080 A | * 9/1983 | Hughes | 526/76 |
| 4,415,714 A | 11/1983 | Mack | |
| 4,426,317 A | 1/1984 | Rogers | |
| 4,433,123 A | 2/1984 | Mack | |
| 4,478,951 A | 10/1984 | Huff | |
| 4,485,186 A | 11/1984 | Ueno et al. | |
| 4,493,903 A | 1/1985 | Mack | |
| 4,493,904 A | 1/1985 | Mack | |
| 4,522,982 A | 6/1985 | Ewen | |
| 4,539,374 A | 9/1985 | Fenton et al. | |
| 4,584,244 A | 4/1986 | Fenton | |
| 4,642,410 A | 2/1987 | Loveless | |
| 4,656,204 A | 4/1987 | Duvdevani et al. | |
| 4,659,685 A | 4/1987 | Coleman, III et al. | |
| H316 H | 8/1987 | Kowalik et al. | |
| 4,693,321 A | 9/1987 | Royer | |
| 4,713,444 A | 12/1987 | Matsuyama et al. | |
| 4,720,397 A | 1/1988 | O'Mara et al. | |
| 4,724,255 A | 2/1988 | Lofgren et al. | |
| 4,756,326 A | 7/1988 | Johnston | |
| 4,758,354 A | 7/1988 | O'Mara et al. | |
| 4,771,799 A | 9/1988 | Baxter et al. | |
| 4,771,800 A | 9/1988 | Pomeroy | |
| 4,789,383 A | 12/1988 | O'Mara et al. | |
| 4,797,461 A | 1/1989 | Aubanel et al. | |
| 4,826,728 A | 5/1989 | O'Mara et al. | |
| 4,837,249 A | 6/1989 | O'Mara et al. | |
| 4,845,178 A | 7/1989 | Hostetler et al. | |
| 4,881,566 A | 11/1989 | Ubels et al. | |
| 4,900,461 A | 2/1990 | Ver Strate et al. | |
| 4,940,682 A | 7/1990 | Sasaki et al. | |
| 4,945,142 A | 7/1990 | Gessell et al. | |
| 4,952,738 A | 8/1990 | Gessell et al. | |
| 4,959,436 A | 9/1990 | Cozewith et al. | |
| 5,070,160 A | 12/1991 | Tomotsu et al. | |
| 5,080,121 A | 1/1992 | Malik et al. | |
| 5,081,087 A | 1/1992 | Villena et al. | |
| 5,104,839 A | 4/1992 | McDaniel et al. | |
| 5,122,584 A | 6/1992 | Takahashi | |
| 5,151,399 A | 9/1992 | Job | |
| 5,162,277 A | 11/1992 | Job | |
| 5,165,441 A | 11/1992 | Mitchell | |
| 5,238,892 A | 8/1993 | Chang | |
| 5,241,025 A | 8/1993 | Hlatky et al. | |
| 5,243,001 A | 9/1993 | Winter et al. | |
| 5,244,937 A | 9/1993 | Lee et al. | |
| 5,276,116 A | 1/1994 | Gessell | |
| 5,276,220 A | 1/1994 | Samsel et al. | |
| 5,278,264 A | 1/1994 | Spaleck et al. | |
| 5,298,474 A | 3/1994 | Luciani et al. | |
| 5,298,579 A | 3/1994 | Hoff et al. | |
| 5,304,614 A | 4/1994 | Winter et al. | |
| 5,310,716 A | 5/1994 | Luciani et al. | |
| 5,320,994 A | 6/1994 | Bujadoux et al. | |
| 5,326,835 A | 7/1994 | Ahvenainen et al. | |
| 5,328,969 A | 7/1994 | Winter et al. | |
| 5,348,925 A | 9/1994 | Milani et al. | |
| 5,349,032 A | 9/1994 | Miyake et al. | |
| 5,350,817 A | 9/1994 | Winter et al. | |
| 5,356,848 A | 10/1994 | Brusson et al. | |
| 5,359,015 A | 10/1994 | Jejelowo | |
| 5,364,994 A | 11/1994 | Scharf | |
| 5,373,072 A | 12/1994 | Chang | |
| 5,374,752 A | 12/1994 | Winter et al. | |
| 5,376,697 A | 12/1994 | Johnston et al. | |
| 5,384,298 A | 1/1995 | Inahara et al. | |
| 5,395,810 A | 3/1995 | Shamshoum et al. | |
| 5,416,176 A | * 5/1995 | Hunt | 526/77 |
| 5,416,178 A | 5/1995 | Winter et al. | |
| 5,416,179 A | 5/1995 | Welch et al. | |
| 5,434,115 A | 7/1995 | Yamada et al. | |
| 5,436,212 A | 7/1995 | Geerts | |
| 5,442,019 A | 8/1995 | Agapiou et al. | |
| 5,449,732 A | 9/1995 | Smith et al. | |
| 5,480,849 A | 1/1996 | Gustafsson et al. | |
| 5,480,948 A | 1/1996 | Geerts | |
| 5,504,131 A | 4/1996 | Smith et al. | |
| 5,504,132 A | 4/1996 | Smith et al. | |
| 5,521,242 A | 5/1996 | Supcoe et al. | |
| 5,539,044 A | 7/1996 | Dindi et al. | |
| 5,541,270 A | 7/1996 | Chinh et al. | |
| 5,574,116 A | 11/1996 | Bujadoux et al. | |
| 5,585,447 A | 12/1996 | Adisson et al. | |
| 5,604,171 A | 2/1997 | Collette et al. | |
| 5,639,842 A | 6/1997 | Tsutsui | |
| 5,644,007 A | 7/1997 | Davidson et al. | |
| 5,668,228 A | 9/1997 | Chinh et al. | |
| 5,705,577 A | 1/1998 | Rossi et al. | |
| 5,710,224 A | 1/1998 | Alt et al. | |
| 5,712,365 A | 1/1998 | Arai et al. | |
| 5,728,855 A | 3/1998 | Smith et al. | |
| 5,733,953 A | 3/1998 | Fairchild et al. | |
| 5,858,904 A | 1/1999 | Takeuchi et al. | |
| 5,869,570 A | 2/1999 | Eaton et al. | |
| 5,932,670 A | 8/1999 | Koppl et al. | |
| 6,015,779 A | * 1/2000 | Eaton et al. | 508/591 |
| 6,126,872 A | 10/2000 | Kommareddi et al. | |
| 6,160,036 A | 12/2000 | Kommareddi et al. | |
| 6,162,773 A | 12/2000 | Eaton et al. | |
| 6,172,151 B1 | 1/2001 | Johnston et al. | |
| 6,178,980 B1 | 1/2001 | Storm | |
| 6,242,395 B1 | 6/2001 | Eaton et al. | |

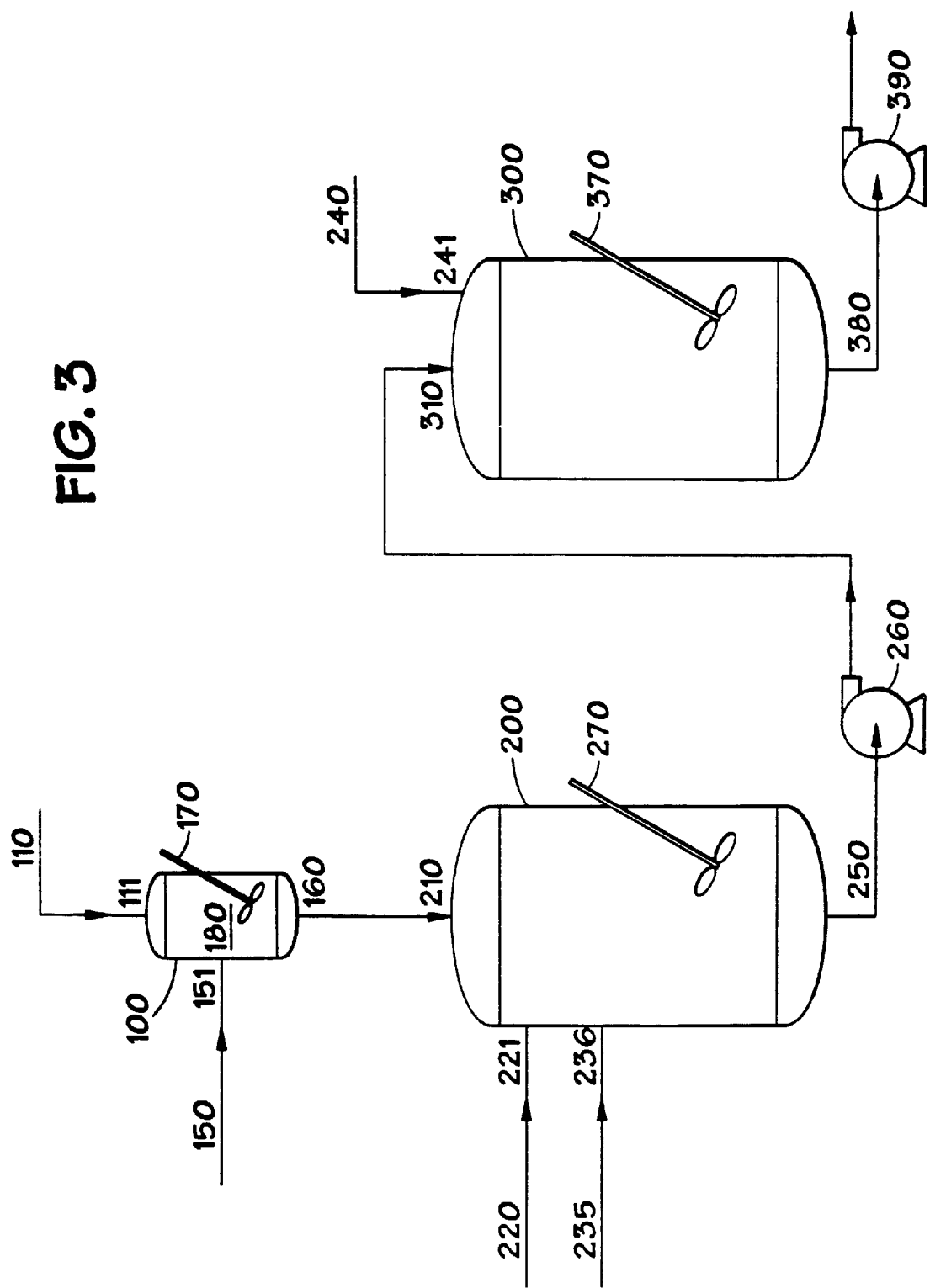

METHODS FOR FORMING AMORPHOUS ULTRA-HIGH MOLECULAR WEIGHT POLYOLEFINS FOR USE AS DRAG REDUCING AGENTS

RELATED APPLICATION

This application claims priority to U.S. Provisional Patent Application Ser. No. 60/261,767, filed Jan. 16, 2001.

BACKGROUND OF THE INVENTION

1. Field of the Invention

This invention relates to methods for forming substantially non-crystalline, ultra-high molecular weight polyolefins which may be used as drag reducing agents for improving flow of hydrocarbons through conduits, particularly pipelines.

2. Description of Related Art

Generally speaking, the flow of liquid in a conduit, such as a pipeline, results in frictional energy losses. As a result of this energy loss, the pressure of the liquid in the conduit decreases along the conduit in the direction of the flow. For a conduit of fixed diameter, this pressure drop increases with increasing flow rate. When the flow in the conduit is turbulent (Reynold's number greater than about 2100), certain high molecular weight polymers can be added to the liquid flowing through the conduit to reduce the frictional energy losses and alter the relationship between pressure drop and flow rate. These polymers are sometimes referred to as drag reducing agents ("DRAs"), and they interact with the turbulent flow processes and reduce frictional pressure losses such that the pressure drop for a given flow rate is less, or the flow rate for a given pressure drop is greater. Because DRAs reduce frictional energy losses, increase in the flow capability of pipelines, hoses and other conduits in which liquids flow can be achieved. DRAs can also decrease the cost of pumping fluids, the cost of equipment used to pump fluids, and provide for the use of a smaller pipe diameter for a given flow capacity. Accordingly, an ongoing need exists to form improved drag reducing materials.

Generally, all commercially viable and available petroleum pipeline drag reducing agents are ultrahigh molecular weight polyalphaolefin polymers that are predominately amorphous, or non-crystalline, are highly and randomly branched polymers produced from various alpha olefin monomers. These particular polymers generally have molecular weights in excess of 15,000,000, and may have molecular weights of 30,000,000 or more.

Polyalphaolefin produced from alpha olefin monomers, generally, incorporate monomer ranging from $C_4$ thru $C_6$ monomers. This particular range of alpha olefin monomers has been found to produce the highest quality and most efficacious DRA polymers. These polymers comprise the substantial bulk of today's commercially available and viable DRA products. In fact, because of the different refining methods utilized by producers of alpha olefin monomers, only one source of alpha olefin monomers (Shell Chemical Company) is recognized by DRA manufacturers as a viable source for producing drag reducing agents. Prior to the present invention, it was not publicly known why this single source of alpha olefin monomers was capable of producing acceptable polymers possessing the desired ultra-high molecular weight and required amorphous or branched structural characteristics for drag reducing agents. Accordingly, the inventors set out to discover a way to use alpha olefin monomers from other suppliers, e.g., Chevron-Phillips Chemical Company, which was previously recognized as an unacceptable source of alpha olefin monomers for drag reducing agents, for the production of DRAs.

In doing so, the inventors hypothesized that the unacceptable alpha olefin monomers produced by all suppliers other than Shell Chemical Company contain trace and objectionable quantities of internal components associated with the production of these alpha olefin monomers that interfere with the formation of the polyalphaolefin during polymerization of the alpha olefin monomers. It is believed that this interference leads to severe technical and commercial limitations including processing/handling and poorer performing DRA that prevent selection of these alpha olefin monomers for production of DRAs.

Accordingly, most, if not all, commercially viable DRAs are produced from alpha olefin monomers manufactured by Shell Chemical Company. As a result, shortages of commercially available quantities of alpha olefin monomers from Shell Chemical Company for the production of DRAs frequently occur. Therefore, prior to the present invention, there was only one source of alpha olefin monomers for the production of drag reducing agents.

SUMMARY OF INVENTION

In one aspect, the present invention is directed to an improvement to methods of increasing the flow of hydrocarbons through conduits, particularly viscous crude oil flowing through pipelines. Surprisingly, it has been discovered that a drag reducing agent (DRA) made in accordance with the methods of this invention provides greater flow improvement when added to a hydrocarbon flowing through a conduit than prior methods. Advantageously, such flow improvement can result when the drag reducing agent's polymer is added to the hydrocarbon at a concentration of as low as 0.25 part per million (ppm) by weight.

In another surprising aspect, it has been discovered that the amount of polymerization catalyst required to produce drag reducing agents is cut in half by isomerizing the olefin monomers prior to polymerization. Therefore, the costs associated with purchasing and storing the polymerization catalyst are reduced.

In certain aspects, the invention also relates to an improvement to methods of producing amorphous, ultra-high molecular weight drag reducing agents having unexpectedly superior drag reduction properties when combined with liquid hydrocarbons, such as viscous crude oil. The improvement comprises isomerizing olefin monomers, and in particular, alpha olefin monomers, prior to polymerization of the olefin monomers to form the polyolefin.

Broadly, one aspect of the invention involves a method of producing an amorphous polyalphaolefin mixture containing an ultra-high molecular weight polyalphaolefin polymer with an inherent viscosity of at least about 10 deciliters per gram and surprisingly superior drag reducing properties when combined with crude oil that is flowing through a pipeline or other conduit. The method preferably includes the steps of isomerizing alpha olefins to form isomerized alpha olefins, contacting a reactant mixture that includes the isomerized alpha olefin monomers with a transition metal catalyst and a co-catalyst to provide an amorphous polyalphaolefin mixture containing an ultra-high molecular weight polyalphaolefin polymer with an inherent viscosity of at least about 10 deciliters per gram and surprisingly superior drag reducing properties when used with viscous crude oil. The polyalphaolefin mixture can be introduced to a pipeline or other conduit having flowing hydrocarbons, such as viscous crude oil. The polyalphaolefin DRA mixture should be introduced in an amount sufficient to increase the flow of the flowing hydrocarbons, preferably at a concentration of from about 1 to 250 ppm by weight, and more preferably from about 5 to 150 ppm by weight.

A specific embodiment of the invention is directed to a method for forming a drag reducing agent comprising a non-crystalline, ultra-high molecular weight polyalphaolefin having an inherent viscosity of at least about 10 deciliters per gram, by isomerizing alpha olefins to form isomerized alpha olefins, contacting the isomerized alpha olefin monomers with a catalyst system that includes a transition metal catalyst and a co-catalyst mixture that includes an alkylaluminoxane co-catalyst; and polymerizing the alpha olefin monomers at a temperature at about or less than about 25° C.; wherein, during the polymerization, at least a portion of the isomerized alpha olefin monomers polymerize in the reactant mixture to provide an ultra-high molecular weight polyalphaolefin.

In another specific embodiment of the invention, the polymerization is terminated by adding a "deactivator" to the reactant mixture after at least a portion of the alpha olefin monomers polymerize in the reactant mixture, to provide an amorphous, ultra-high weight polyalphaolefin. One example of a deactivator is a mixture of isopropyl alcohol and butylated hydroxytoluene.

A variety of alpha olefin monomers are useful in this invention, including homopolymers, copolymers and terpolymers, which, after isomerization, can be present in the reactant mixture in different amounts, alone or in combination. Preferably, these monomers are isomerized and introduced into the reactant mixture at a charge rate of about 4% to 22% based on total weight of the reactant mixture. Charge rate is herein defined as the weight percent of total charge, including one or more components, e.g., solvent, co-catalyst, catalyst, and isomerized alpha olefin monomers. More preferably, the isomerized alpha olefin monomers are present at a charge rate of 4% to 99.5% based on total weight of the reactant mixture.

Examples of alpha olefin monomers that are useful in this invention are co-monomers of 1-hexene and 1-dodecene alpha olefins; or co-monomers of 1-octene and 1-tetradecene alpha olefins in a 1:1 ratio based upon mole weight of the monomers.

A preferred transition metal catalyst is titanium trichloride, which is preferably present in the reactant mixture in an amount of from about 50 to about 1500 parts per million, preferably from about 75 to about 400 parts per million, based on the total weight of all the reactants or components in the reactant mixture.

A further feature of the process for forming a drag reducing agent comprising a non-crystalline, ultra-high molecular weight polyalphaolefin having an inherent viscosity of at least about 10 deciliters per gram is that the reactant mixture may include at least one hydrocarbon solvent such that the isomerized alpha olefin monomers and polyalphaolefin remain substantially dissolved in the hydrocarbon solvent. An additional feature of the process is that the polymerization of the isomerized alpha olefin monomers continues such that the polyalphaolefin is present in the reactant mixture at a concentration of at least about 4 weight percent based upon the weight of the reactant mixture and the polyalphaolefin having an inherent viscosity of at least about 10 deciliters per gram is formed in less than about 24 hours. Another feature of the process is that the polyalphaolefin has an inherent viscosity of at least about 10 deciliters per gram and is amorphous with substantially no crystalline particles. A further feature of the process is that the flow increase is at least about 30% when the polyalphaolefin is present in hexane at a weight concentration of 1 part per million. Another feature of the process is that the catalyst system may include dibutylaluminum chloride and/or diethylaluminum chloride.

In another specific embodiment, the present invention includes a drag reducing agent comprising a non-crystalline, ultra-high molecular weight polyalphaolefin having an inherent viscosity of at least 10 deciliters per gram, formed by isomerizing alpha olefin monomers to form isomerized alpha olefin monomers, contacting the isomerized alpha olefin monomers with a catalyst system in a reactant mixture, wherein the catalyst system includes a transition metal catalyst, such as titanium trichloride, and the co-catalyst mixture includes an alkylaluminoxane co-catalyst, such as methylaluminoxane and isobutylaluminoxane; and polymerizing the isomerized alpha olefin monomers at a temperature at about or less than 60° C., preferably less than 40° C., wherein during the polymerization, at least a portion of the isomerized alpha olefin monomers polymerize in the reactant mixture to provide a non-crystalline, ultra-high molecular weight polyalphaolefin.

In yet another specific embodiment, the present invention includes a process for reducing drag in a conduit by forming a drag reducing agent comprising a non-crystalline, ultra-high molecular weight polyalphaolefin, by isomerizing alpha olefin monomers to form isomerized alpha olefin monomers, contacting the isomerized alpha olefin monomers with a catalyst system in a reactant mixture, wherein the catalyst system includes a transition metal catalyst and an alkylaluminoxane co-catalyst; polymerizing the isomerized alpha olefin monomers at a temperature at about or less than 60° C., preferably less than 40° C.; wherein during the polymerization, at least a portion of the isomerized alpha olefin monomers polymerize in the reactant mixture to provide a non-crystalline, ultra-high molecular weight polyalphaolefin having an inherent viscosity of at least 10 deciliters per gram; and introducing the drag reducing agent into the conduit.

In still another aspect of the invention, a halohydrocarbon co-catalyst may be used in conjunction with a transition metal catalyst to form the drag reducing agent. For example, another specific embodiment of the invention is directed to a process for forming a drag reducing agent comprising a non-crystalline, ultra-high molecular weight polyalphaolefin having an inherent viscosity of at least about 10 deciliters per gram. The process includes the steps of isomerizing alpha olefin monomers to form isomerized alpha olefin monomers, contacting the isomerized alpha olefin monomers with a catalyst system in a reactant mixture, wherein the catalyst system includes a transition metal catalyst and a co-catalyst mixture having at least two co-catalysts, wherein one of the co-catalysts preferably is a halohydrocarbon. More preferably, the co-catalyst mixture also includes alkylaluminoxane. The isomerized alpha olefin monomers are polymerized at a temperature at about or less than 60° C., wherein during the polymerization, at least a portion of the isomerized alpha olefin monomers polymerize in the reactant mixture to provide a non-crystalline, ultra-high molecular weight polyalphaolefin.

A further feature of the process for forming a drag reducing agent comprising a non-crystalline, ultra-high molecular weight polyalphaolefin having an inherent viscosity of at least about 10 deciliters per gram is that the halohydrocarbon is preferably a chloride containing halohydrocarbon such as ethylene dichloride. Another feature of the process is that the transition metal catalyst is preferably titanium trichloride. An additional feature of the process is that the catalyst system preferably includes an alkylaluminoxane such as methylaluminoxane and/or isobutylaluminoxane.

BRIEF DESCRIPTION OF THE DRAWINGS

FIG. 3 is a flow diagram of a two-stage continuous process.

DETAILED DESCRIPTION OF THE INVENTION

Figure 2:
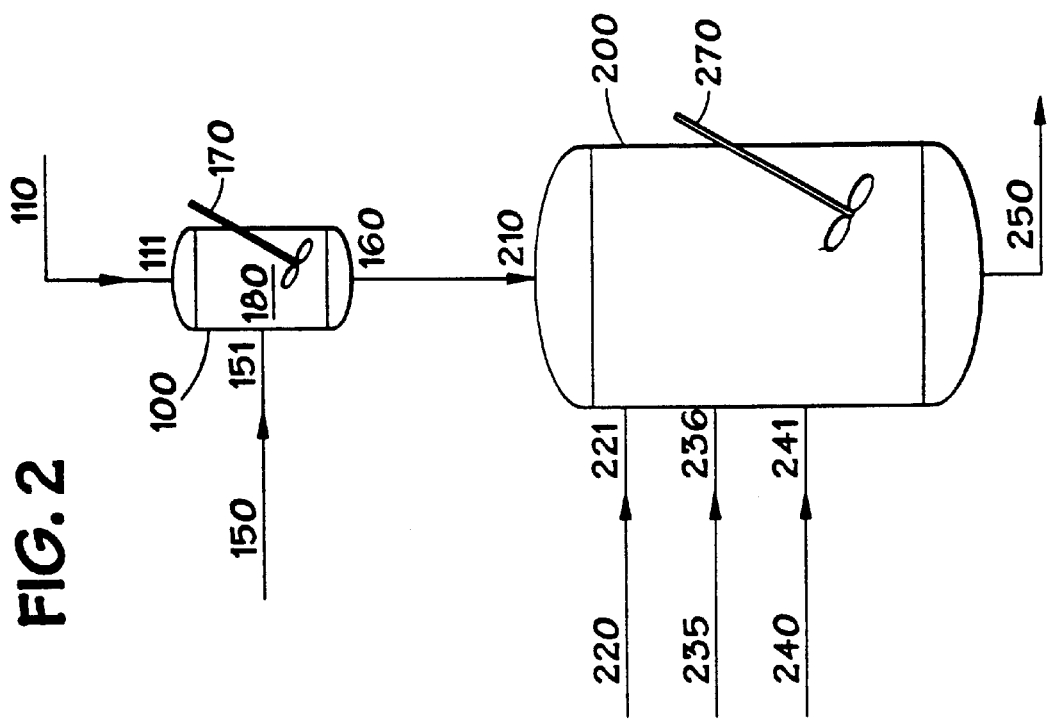
FIG. 2 is a flow diagram of a single-stage continuous process.

As mentioned above, the present invention is directed to the formation of improved drag reducing agents formed by isomerization of olefins. The improvement comprising isomerizing olefins monomers, and preferably, alpha olefin monomers, to form isomerized olefin monomers. Isomerized olefin monomers are herein defined as olefin monomers having substantially all hydrocarbon branches removed, i.e., substantially all of the olefin monomers are straight chained olefin monomers.

It is contemplated that any isomerization process which converts substantially all of the branched olefins into straight olefins may be utilized in accordance with the present invention. In the preferred embodiment, isomerization of alpha olefin monomers may be performed by the process disclosed in U.S. Pat. No. 4,697,040, which is hereby incorporated by reference. Isomerization of alpha olefin monomer feedstocks containing mostly vinyl olefins and minor amounts of vinylidene olefins has been found to be a suitable olefin feedstock for isomerization and subsequent polymerization to form drag reducing agents. While it is not fully understood by the inventors why isomerization of alpha olefin monomers prior to polymerization produces a polyalphaolefins capable of reducing drag in a conduit, it is contemplated that isomerization of the alpha olefin monomers removes, alters, or reduces the functionality of vinyl olefins and vinylidene olefins present in some alpha olefin feedstocks.

Briefly, isomerization of the olefins may be performed by contacting an olefin feedstock with a catalyst comprising LZ-Y52 zeolite under olefin isomerization reaction conditions disclosed in U.S. Pat. No. 4,697,040. Preferred feedstocks for forming drag reducing agents in accordance with the present invention are $C_6$ to $C_{10}$ olefinic feedstocks containing at least 90 wt % vinyl olefins and containing 10 to 0.1 wt % vinylidene olefins. The preferred feedstocks include individual olefin cuts within the $C_6$ to $C_{10}$ range, such as $C_6$, $C_7$, $C_8$, $C_9$ or $C_{10}$ cuts, or mixtures of two or more of the foregoing, or the entire $C_6$ to $C_{10}$ range. More preferred alpha olefins include an 1-octene feedstock containing 2-ethyl-hexene-1. In this application the 2-ethyl-hexene-1 is isomerized, at least in part, to 3-methyl-heptene-2 and 3-methyl-heptene-3.

Thus, according to a more preferred embodiment of this isomerization step in forming drag reducing agents, the feedstock to the isomerization step is at least 95 wt % 1-octene containing 5 to 0.1% 2-ethyl-hexene-1, and at least 50% of the 2-ethyl-hexene-1 is isomerized to 3-methyl-heptene-2 and 3-methyl-heptene-3 while no more than 5%, generally less than 1%, of the 1-octene is lost to side reaction products.

The catalyst used in this preferred embodiment of the isomerization step of the process of the present invention is a LZ-Y52 zeolite catalyst material commercially available from Union Carbide Corporation. LZ-Y52 is described in Sales Bulletins by Union Carbide, for example, Bulletin F-3858B, 1500, 3/78, 88-0258. The LZ-Y52 material is a synthetic crystalline aluminosilicate of a cubic arrangement having a density of 1.3 g/cc and having the following formula:

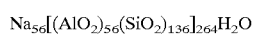

LZ-Y52 can be made in, and also is commercially available in, various shapes. For example, LZ-Y52 is available as ⅛ inch or 1/16 inch extrudate pellets.

The LZ-Y52 material is a Y-type zeolite. Y-type zeolites are well known in the art, see for example, D. W. Breck, "Crystalline Molecular Sciences", J. of Chem. Ed., Vol. 41, No. 12, December 1964, pp. 678–689, which disclosure is incorporated herein by reference. As noted by Breck, the composition of the Y zeolite is $Na_{56}[(AlO_2)_{56}(SiO_2)_{136}]_{264}H_2O$; the symmetry and cell dimension is cubic with a=24.7 Angstroms; the density is 1.3 g/cc; the void volume is 0.35 cm³/g; the aperture size is 8 Angstroms and the structure is pictorially shown in FIG. 9 in the cited Breck reference. Amongst other factors, zeolite Y differs from zeolite X in that the formula for zeolite X is $Na_{56}[(AlO_2)_{86}(SiO_2)_{106}]_{264}H_2O$.

LZ-Y52 has been described as a Y zeolite, in particular a sodium Y zeolite, which is an excellent starting material if high ion exchange capacity is desired. LZ-Y52 can be converted to LZ-Y62 by cation exchange of ammonium for sodium, with the sodium content of LZ-Y52 reduced by 80%. The chemical and physical properties of LZ-Y52 compared to LZ-Y62 are as follows: $Na_2O$, 13 wt % vs 2.5 wt % for LZ-Y62; $(NH_4)_2O$, none vs 9.8 wt % for LZ-Y62; $Na^+$ to Al molar ratio, 0.934 vs 0.18 for LZ-Y62; $NH_4^+$ to Al ratio, none vs 0.862 for LZ-Y62; $O_2$ capacity, 33.6 wt % vs 34.0 for LZ-Y62; and cell dimension "a" of 24.68 for LZ-Y52 vs 24.73 for LZ-Y62.

Suitable temperatures for use in the isomerization process of the preferred embodiment are between 10° C. and 150° C. preferably between 30° C. and 120° C. and more preferably between 35° C. and 100° C. Suitable pressures for use in the isomerization process of the present invention are between 1 and 5000 psia more preferably between 10 and 100 psia and most preferably between 15 and 45 psia.

Suitable weight hourly space velocities (WHSV) for use in the isomerization process of the present invention are between 0.1 and 100, preferably between 1 and 50, and most preferably between 2 and 20. The WHSV is computed as the weight of feed per hour to the reactor divided by the weight of catalyst in the reactor.

As stated above, the process of the present invention is applied to feedstocks containing mostly vinyl olefins, but with minor amounts of vinylidene olefins also present. The amount of vinyl olefins in the feed generally is at least 80 wt %, preferably 90 wt % and more preferably at least 95 wt %. The amount of vinylidene is generally less than 20 wt %, preferably less than 5 wt %, and more preferably less than 3 wt %, for example 1/10 to 3 wt % of vinylidene olefins.

Minor amounts of other olefins and non-olefinic materials may also be present in the basically vinyl olefin feedstock material.

A typical source of the vinyl olefin feedstock containing minor amounts of vinylidene olefins is a Ziegler ethylene growth reaction for producing higher olefins such as $C_6$–$C_{10}$ olefins.

ISOMERIZATION EXAMPLE 1

A one-inch inside diameter pipe was filled to a depth of five inches with an inert bed of quartz (preheat section) and then with six inches of LZ-Y52 catalyst (62 g). 1-octene containing 1.68% 2-ethyl-hexene-1 was then pumped upflow through the pipe at a rate of 124 g per hour. The results for the first 165 hours of operation are shown by the data points in Table 1. The rate was increased to 248 g per hour for the last two data points. Samples were taken with the periodicity shown in the table and analyzed by gas chromatography.

A 13-X zeolite was also evaluated in the same manner (same operating conditions as above except different catalyst) with the first sample being taken after 48 hours at 48° C. This sample contained 1.68% 2-ethyl-hexene-1 (vinylidene). Initially, the 13-X zeolite, an X-type zeolite, had provided some isomerization of the vinylidene, but after 48 hours, the catalyst run-life for this application had been exceeded.

The percent "cis-2" shown in Table I is the percent of cis structure 2-olefins unbranched olefins in the product. The amount of trans-2-olefins is approximately one and one-half times the cis 2-olefins. The data thus shows that, using the LZ-Y52 catalyst, a high percent of the vinylidene olefins was converted to non-vinylidenes without losing much of the 1-octene to internal olefins and with a relative long catalyst run-life achieved.

TABLE I

VINYLIDENE ISOMERIZATION OVER LZ-Y52

| Time (h) | WHSV | g Prod/g Catalyst | % Vinylidene | % Cis-2 | Temp. (° C.) |
|---|---|---|---|---|---|
| 0 | — | — | 1.68 | 0.04 | — |
| 4 | 2 | — | 0.04 | 0.10 | 48 |
| 24 | 2 | 48 | 0.04 | 0.14 | 45 |
| 32 | 2 | — | 0.04 | 0.06 | 45 |
| 48 | 2 | 96 | 0.10 | 0.04 | 32 |
| 72 | 2 | 144 | 0.20 | 0.03 | 28 |
| 165 | 2 | 330 | 0.07 | 0.04 | 42 |
|  | 4 | — | 0.24 | 0.04 | 53 |
| 200 | 4 | 450 | 0.12 | 0.07 | 69 |

ISOMERIZATION EXAMPLE 2

In another example, alpha olefin monomers are isomerized into isomerized alpha olefin monomers by placing the catalyst LZ-Y52 into an isomerization unit to create a catalyst bed within the isomerization unit that has a height to width ratio of at least 1:1, and preferably, having a height to width ratio of at least 2:1. Alpha olefin monomers are then charged to the isomerization unit by passing the alpha olefin monomers through the catalyst bed. In this embodiment, the charge rate of the alpha olefin monomer through the catalyst bed is in the range from about 8 pounds per minute to about 40 pounds per minute per hour at a temperature in the range from about 15° C. to about 110° C.

After the alpha olefin monomers are isomerized, they are charged to a reactor for polymerization. It is contemplated that any polymerization process may be utilized to polymerize the isomerized alpha olefin monomers into polyalphaolefin drag reducing agents. In the preferred embodiment, the isomerized alpha-olefin monomers are polymerized to form drag reducing agents using the polymerization process disclosed in U.S. Pat. No. 6,015,779, which is hereby incorporated by reference. For purposes of better understanding the preferred polymerization step of the present invention, certain terms will now be explained and defined.

Drag Reducing Agents.

The term "drag reducing agent" (DRA) as used herein refers to a composition that includes at least the formed polyalphaolefin polymer, preferably made in accordance with the methods described herein. Preferably, because the polyalphaolefin polymer of this invention is can be fully dissolved in the solvent, the "DRA" can also refer to the entire reactant mixture after sufficient polymerization has occurred (also referred to as a "polymerization mixture"), including not only the polyalphaolefin, but also the solvent, any viscosity reducing agents and any unreacted monomers. The DRA can also include any remaining transition metal catalyst and co-catalyst. Additionally, the "DRA" can also refer to the polyalphaolefin particles suspended in a liquid to form a drag reducing agent slurry.

The term "polyalphaolefin" refers to the polymer material formed by the polymerization of the alpha olefin monomers, and is broadly construed to include not only the polymer in its final form, e.g., polyalphaolefin having an ultra-high molecular weight and inherent viscosity of 10 deciliters per gram or greater, but also any intermediate polymers being formed, sometimes referred to as "oligomers."

Flow Increase.

A preferred aspect of the present invention is directed to "flow increase" or "drag reduction." As discussed below, drag reducing agents reduce drag and increase the flow rate of hydrocarbons passing through conduits, particularly crude oil or refined hydrocarbons passing through pipelines. In at least one aspect, the DRA can be introduced into the conduit to improve flow conditions by reducing frictional pressure losses, or frictionally generated energy bursts, associated with movement of fluid within the conduit. These frictionally generated energy bursts typically emanate from throughout the turbulent core of the flowing hydrocarbons and include lateral turbulent microbursts generated from or near the conduit walls. More simply stated, the DRAs tend to reduce the impact of turbulence through direct interaction and absorption of some or most of these energy bursts thus improving flow characteristics in the conduit. It has been discovered that a DRA should have the right combination of properties to provide superior drag reduction and flow improvement. For example, the DRA should be non-crystalline and amorphous, preferably having substantially no solid particles. The DRA also should have an ultra-high molecular weight, as discussed above. Finally, the DRA needs to provide superior flow improvement. In this respect, it has been observed by the inventors that the mere fact that a polymer is amorphous and has a very high molecular weight does not necessarily make it useful for flow improvement. The superior properties of the DRA of this invention are thus both surprising and unexpected.

Accordingly, one of the more important aspects of the invention is the superior "flow increase" or "drag reduction" provided by the DRA That is, when combined in sufficient quantities with a hydrocarbon flowing through a conduit, the DRA of this invention provides a flow increase that is superior to the flow increases provided by other commercially available DRAs. Although flow increase can be defined in qualitative terms, it can also be quantified, for comparison purposes, by using an empirical test sometimes called a "Percent Flow Increase" test, calculated using the following equation:

$$\text{Percent Flow Increase} = \frac{W_1 - W_0}{W_0} \times 100\%$$

As discussed below in the Examples, Percent Flow Increase measurements were taken of certain samples of invention DRA and also of certain comparative DRA samples. Both 1" and ¼" diameter hydraulic flow loops were used herein to measure Percent Flow Increase. The value "$W_0$" refers to the weight of a test sample of hydrocarbon without any DRA present, while the term "$W_1$" refers to the weight of a test sample of hydrocarbon with a predetermined amount of DRA present.

In either case, the weight of the test sample is determined by carefully weighing the amount of hydrocarbon that passes through the flow loop over a constant time interval. The time interval is dependant upon the total weight of DRA treated hydrocarbon which is passed through the flow loop. In the 1" flow loop, this weight is typically greater than 150 pounds of DRA treated hydrocarbon. In the ¼" flow loop, this weight is typically about 1 pound of DRA treated hydrocarbon.

Similarly, another quantitative method of measuring drag reduction, and particularly for comparing different DRAs, is measuring "Percent Drag Reduction" (% DR) which is calculated using the following equation:

$$\text{Percent Drag Reduction} = \frac{P_1 - P_0}{P_0} \times 100\%$$

The term "$P_0$" refers to the measured pressure drop occurring when pure hexane (without DRA) is pumped through a flow loop. The term "$P_1$" refers to the measured pressure drop occurring when hexane (treated with DRA) is pumped through the flow loop. Percent Drag Reduction (% DR) is also discussed in the Examples.

Ultra-High Molecular Weight.

Another important aspect of this invention is that the polyalphaolefin polymer must have an "ultra-high molecular weight," a term defined herein as a molecular weight corresponding to an inherent viscosity of at least about 10 deciliters per gram. Because of the extremely high molecular weight of the DRA polymer, it is difficult to reliably and accurately measure the actual molecular weight, but inherent viscosity provides a useful approximation of molecular weight. For purposes of the present invention, "inherent viscosity" is measured using a Cannon-Ubbelohde four bulb shear dilution viscometer (0.1 g polymer/100 ml toluene at 25° C.). Inherent viscosities are calculated for each of the four bulbs. The viscosities are then plotted as a function of shear rate. The plot is then used to determine the inherent viscosity at a shear rate of 300 sec-1. It is contemplated that an inherent viscosity of 10 deciliters per gram corresponds roughly to a molecular weight of at least about 10 or 15 million. Preferably, the ultra-high molecular weight polyalphaolefins of the present invention have molecular weights even higher, e.g., greater than 25 million. The polyalphaolefins formed should also have a narrow molecular weight distribution. Because different assumptions about the properties of the polyalphaolefin can yield different estimates of molecular weights, the inventors prefer using inherent viscosity to characterize the molecular weights of their drag reducing agents.

Amorphous.

Yet another property of the polyalphaolefin made in accordance with the invention is its substantially non-crystalline nature. The polyalphaolefin can be liquid or solid. In one specific embodiment, the polyalphaolefin is liquid and is soluble in the hydrocarbon solvent used as discussed herein, so that a single liquid phase reactant mixture is provided. In this embodiment, the polyalphaolefin is amorphous, having no crystalline structures, or habits, existing in a single phase with substantially no solid particles. Preferably, in this specific embodiment, during the polymerization process, the polyalphaolefin being formed fully dissolves into the solvent, providing a single-phase DRA that can be used without the need to conduct any separation procedures. Furthermore, another advantage of this single-phase DRA is that it can be conveniently tested for quality purposes. Moreover, this DRA has a long stable shelf life.

In another specific embodiment, the polyalphaolefin is solid forming a "polyalphaolefin block" and can be added directly to a conduit containing a hydrocarbon stream. Alternatively, the solid polyalpholefin can be cryoground and suspended in a liquid to form a drag reducing agent slurry that can then be added to a conduit containing a hydrocarbon stream.

Catalyst System.

The "catalyst system," as defined herein, includes a transition metal catalyst and a co-catalyst mixture. In a preferred embodiment. The co-catalyst system contains an alkylaluminoxane co-catalyst. The transition metal catalyst and the alkylaluminoxane co-catalyst can be combined with the alpha olefin monomer in a number of ways. The transition metal catalyst and alkylaluminoxane co-catalyst are preferably combined with the monomer at the same time. They are preferably mixed together before the polymerization reaction is initiated. Preferred transition metal catalysts include catalysts containing titanium trichloride, titanium tetrachloride or metallocene or combinations thereof. Preferably, the transition metal catalysts are non-metallocene. Titanium trichloride, which is most preferred, has been used for years in making drag reducing agents, and is preferably used in an amount ranging from at least about 100 to 1500 parts per million (ppm) based on the weight of all the components, i.e., the alpha olefins, solvents, co-catalysts, and catalysts supplied to the reactor. The co-catalyst mixture may include alkylaluminoxane alone, or may also include at least one other component, such as diethylaluminum chloride ("DEAC") or dibutylaluminum chloride ("DIBAC"). In a highly preferred aspect of the invention, other co-catalysts that provide excellent results are halohydrocarbons, such as ethylene dichloride used either alone, or in combination with an alkylaluminoxane co-catalyst.

Alkylaluminoxane.

In one specific embodiment, a component that provides the polyalphaolefin for combining with hydrocarbons (e.g., crude oil) is alkylaluminoxane, preferably either methylaluminoxane (MAO) or isobutylaluminoxane (IBAO). Alkylaluminoxane is a compound having a plurality of aluminum atoms, typically formed by a condensation reaction in which a trialkylaluminum compound (e.g., trimethylaluminum) is combined with a condensing agent, such as water (i.e., resulting in hydrolysis). It is noted, however, that the present invention is not concerned with how to actually make the alkylaluminoxane, which is commercially available from a variety of sources, for example, AKZO NOBEL Chemical Inc., Chicago, Ill.

In addition to MAO and IBAO, it is contemplated that other alkylaluminoxanes can also be used, including chain alkylaluminoxanes and cyclic aluminoxanes. A chain aluminoxane has the following general structure, wherein $R^1$ is an alkyl group and n is the polymerization degree:

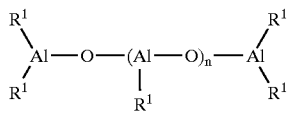

A cyclic alkylaluminoxane is a long-chained compound having a chemical structure formed by repeating units having the following structure, wherein $R^1$ is an alkyl group:

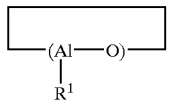

The concentration of the alkylaluminoxane in the co-catalyst mixture is preferably in the range of at least about 100 to about 3500 parts per million (ppm), based on the weight of all the components in the reactant mixture. More preferably, the concentration of the alkylaluminoxane in the catalyst mixture is from at least about 800 to about 2000 ppm.

Halohydrocarbon.

Another surprising discovery relates to the use of one or more halohydrocarbons as co-catalysts. "Halohydrocarbons" are herein defined as compounds having the formula $R-X_n$, wherein X is a halogen, n is the number of halogen atoms, and R is a hydrocarbon group such as aromatic and aliphatic hydrocarbons, including alkanes, alkenes, acetylenes, or any other hydrocarbon known to persons skilled in the art which may be combined with one or more halogens in accordance with the formula $R-X_n$. In a specific embodiment, the X is chloride, n is 2, and R is an alkane. More preferably, the halohydrocarbon is ethylene dichloride.

Specifically, it has also been discovered that using a halohydrocarbon as a co-catalyst, particularly in combination with an alkylaluminoxane co-catalyst, provides polyalphaolefins with superior flow improving properties when compared to other drag reducing agents. Chloride containing halohydrocarbons are preferred. Although only theoretical at this point, it is contemplated that the chloride containing halohydrocarbons act as chloride donors which promote polymerization of alpha olefins.

The halohydrocarbon is preferably combined with an alkylaluminoxane and titanium trichloride catalyst to form a catalyst system, e.g., a slurry. It is contemplated that, in a specific embodiment, dibutylaluminum chloride and/or diethylaluminum chloride may also be included in the catalyst slurry. The catalyst system is then mixed with the alpha olefin monomers. It has been discovered that polymerization of the alpha olefin monomers in the presence of the halohydrocarbon forms a polyalphaolefin which has improved drag reducing capabilities.

Perhaps the most surprising result arising from the use of a co-catalyst mixture utilizing both ethylene dichloride and alkylaluminoxane is its impact on polymerization rates. For example, typical Ziegler-Natta polymerization processes require approximately 15 to 70 hours of polymerization time to form a weight percent polyalphaolefin having drag reducing characteristics. By comparison, using ethylene dichloride as a co-catalyst, the rate of polymerization is increased dramatically such that the weight percent of the polyalphaolefin in the reactant mixture may be formed in less time. For example, a reactant mixture having a selected weight percent polyalphaolefin as a reference may be formed in under 12 hours. Preferably, a 5 weight percent polyalphaolefin may be formed in under 7 hours, and more preferably, in under 5 hours. Such a rapid rate of polymerization is a dramatic improvement over the current procedures for forming drag reducing agents.

In a specific embodiment of the invention, a drag reducing agent comprising a non-crystalline, ultra-high molecular weight polyalphaolefin having an inherent viscosity of at least about 10 deciliters per gram is formed by contacting alpha-olefin monomers with a catalyst system in a reactant mixture. The catalyst system includes a transition metal catalyst, such as titanium trichloride, and a co-catalyst mixture having at least two co-catalysts, wherein one of the co-catalysts is a halohydrocarbon. While it is contemplated that any halohydrocarbon co-catalyst may be utilized, preferably, the halohydrocarbon co-catalyst is either an alkyl halide or an alkyl dihalide, and more preferably is an alkyl dihalide. Preferably the halogen atom of the halohydrocarbon is chloride, and the most preferred halohydrocarbon is ethylene dichloride. An alkylaluminoxane co-catalyst such as methylaluminoxane and/or isobutylaluminoxane is preferably included in the catalyst system.

The alpha olefin monomers should be polymerized at a temperature at about or less than 60° C., and preferably, at about or less than 40° C., wherein during the polymerization, at least a portion of the alpha olefin monomers polymerize in the reactant mixture to provide a non-crystalline, ultra-high molecular weight polyalphaolefin. Preferably, the alpha olefin monomers are polymerized at a temperature of about −5° C. The ethylene dichloride co-catalyst should be present in the reactant mixture at a concentration ranging from at least about 50 weight ppm based upon the weight of all the reactants in the reactant mixture to about 200 weight ppm. Preferably, the ethylene dichloride is present in the reactant mixture at a concentration ranging from at least about 80 weight ppm to about 120 weight ppm.

Reactant Mixture.

Generally, the reactant mixture includes alpha olefin monomers and solvent, which is then combined with the "catalyst system," discussed above. Useful alpha olefin monomers broadly include any that are capable of forming a polyalphaolefin with the desired properties discussed herein. Preferably, the alpha olefins have 2 to 20 carbon atoms.

Homopolymers, copolymers and terpolymers may be used. Preferred alpha olefins include ethylene, propylene, 1-butene, 4-methyl-1-pentene, 1-hexene, 1-octene, 1-decene, 1-dodecene and 1-tetradecene; conjugated or unconjugated dienes such as butadiene and 1,4-hexadiene; aromatic vinyls such as styrene; and cyclic olefins such as cyclobutene. Most preferably, the alpha olefin monomers are co-monomers of 1-hexene and 1-dodecene present in a 1:1 mole ratio; or co-monomers of 1-octene and 1-tetradecene present in a 1:1 mole ratio. The alpha olefin monomers can be present in the reactant mixture at a charge rate of 4% to 22% based upon the total weight of the reactant mixture, or more preferably, at a charge rate of 4% to 20%.

Polymerization.

Liquid phase polymerization is one technique for forming the DRA polyalphaolefins of this invention, as discussed below in greater detail. In liquid phase polymerization, the monomers and polymers are both completely dissolved in the solvent. It is critical that substantially no solid phase particles are formed. It is contemplated, however, that a variety of other polymerization reactions can form the DRA polyalphaolefins of this invention, including, for example, gas phase polymerization, bulk polymerization, suspension polymerization and emulsion polymerization. These polymerization procedures are relatively conventional, and are generally either known by persons skilled in the art; readily ascertainable from the patent and technical literature; or can be arrived at without excessive experimentation. Additionally, either batch or continuous polymerization methods can be used, in either one or multiple stages. Furthermore, the various reactants may be added to the reactant mixture in numerous ways, all which are known to persons skilled in the art. For example, the alpha olefin monomers and hydrocarbon solvent may be combined together in a storage tank and stored until the polymerization process is initiated by the addition of the catalyst and co-catalyst mixture. Alternatively, the catalyst and the alpha olefins may be combined in advance of adding the hydrocarbon solvent and the co-catalyst from separate sources. Preferably, as discussed below, the catalyst system including transition metal catalyst and one or more co-catalysts is formed first and then combined with the alpha olefin monomers and the hydrocarbon solvent from separate sources.

Batch liquid phase polymerization is another technique for forming the DRAs of this invention. Because relatively low temperatures are involved, insulated reaction vessels are used. The temperature of the reactant mixture is preferably maintained at about 25° C. or less, preferably, at about 10° C. or less. The pressure of the reaction mixture is not critical, and is usually in the range of from about atmospheric pressure to about 1500 psig. The polymerization is conducted under conditions such that the polyalphaolefin being formed will have an inherent viscosity of about at least 10 deciliters per gram (dL/g). The time for the polyalphaolefin to reach that inherent viscosity depends largely on the catalyst system, reaction conditions and the concentration of monomers being polymerized.

A catalyst system can be prepared by first mixing the appropriate amount of transition metal catalyst (e.g., titanium trichloride) with the respective liquid co-catalysts. This catalyst system is then directed to a storage vessel where the catalyst system may be stored, or aged or conditioned, for a time sufficient to optimize the efficaciousness of the catalyst system. Preferably, the catalyst system is stored for at least about 6 to about 72 hours. More preferably, the catalyst system is stored for at least about 10 to about 30 hours. To begin the polymerization reaction, the catalyst system can be metered from this storage vessel into the first reactor where it is mixed in desired proportions with the alpha olefin monomers.

In a batch process, polymerization can be initiated in a first reactor at an appropriate temperature and pressure. After polymerization progresses for a predetermined period of time, e.g., long enough to form a certain amount of polyalphaolefin polymer with a certain molecular weight and molecular weight distribution as determined by, e.g., inherent viscosity, the polyalphaolefin mixture can be transferred to a second reactor, where polymerization continues, until the polyalphaolefin mixture has the desired final inherent viscosity via monomer to polymer conversion. After this transfer takes place, fresh starting ingredients can be added to the first reactor, including new amounts of catalyst system containing alkylaluminoxane co-catalyst and unreacted alpha olefins.

Alternatively, two reactors can be used in a continuous process. During start-up, the starting ingredients, i.e., the alpha olefin monomer reactants, a transition metal catalyst, co-catalyst mixture are added to the first reactor. After a period of time, the monomers in the first reactor form a predetermined minimum amount of oligomers and fully-formed polyalphaolefin polymers. A portion of the oligomers and polymers are then continuously pumped into the second reactor, at a predetermined rate and mixed with a hydrocarbon solvent. The hydrocarbon solvent enhances the ability of the DRA to become incorporated or dissolved into the hydrocarbons, e.g., the crude oil in a pipeline. While it is contemplated that any hydrocarbon solvent may be employed which enhances the DRA's incorporation into the hydrocarbon, suitable hydrocarbon solvents include aromatic and aliphatic hydrocarbons, butanes, propanes, isopentanes, and other mixed liquid propane gas and natural gas liquids. Preferably, all acceptable solvents must not contain more than trace amounts (i.e., less than about 5 ppm) of sulfur or sulfur containing compounds.

Simultaneously, new starting ingredients are pumped into the first reactor, eventually reaching a steady state balance between the incoming ingredients and the outgoing oligomer/polymer mixture. Preferably, the flow of material into and out of the first reactor is controlled to maintain a relatively constant average molecular weight and narrow molecular weight distribution of the polyalphaolefin, e.g., as reflected by inherent viscosity. The resident time of the reactant mixture in the second reactor can be varied in accordance with the desired final molecular weight and molecular weight distribution of the polyalphaolefin. The average molecular weight of the polyalphaolefins in the reactant mixture in the second reactor tend to be far greater than that of the oligomer/polymer mixture in the first reactor. Additional reactors can also be used, depending on the design of the system.

As mentioned above, the polymerization of the alpha olefin monomers is conducted in the presence of a catalyst system, which includes a transition metal catalyst and a co-catalyst mixture. The catalyst and co-catalysts may be added as initial raw ingredients or they may be added as additives at any time during the polymerization process. Preferably, the catalyst and co-catalysts are added to the polymerization reaction mixture at the same time alpha olefin monomers are added. Alternatively, in a two-stage process, the catalyst and the co-catalyst mixture are added at any time during actual polymerization, i.e., in the absence of "catalyst killers" or any other polymerization-terminating ingredient.

Preferably, the process is carried out in the presence of excess monomers to provide a process which does not end due to the exhaustion of monomers. In a preferred embodiment, the process is halted by the addition of deactivators, or catalyst inhibitors, such as a mixture of isopropyl alcohol and butylated hydroxytoluene, after a sufficient amount of polyalphaolefin is produced by the polymerization reaction. The addition of the catalyst inhibitors terminates the polymerization reaction in advance of full monomer conversion and provides selective capture of polyalphaolefins having the desired properties including desired molecular weight and molecular weight distribution. Isopropyl alcohol may be added to the reactant mixture at a concentration of from about 0.1 weight percent to about 1 weight percent. Preferably, the isopropyl alcohol is added to the reactant mixture at a concentration of about 0.25 weight percent. Butylated hydroxytoluene may be added in small amounts to the isopropyl alcohol as a preservative and/or antioxidant. Butylated hydroxytoluene may be added to the reactant mixture as a component mixture in the isopropyl alcohol at a concentration of from about 0.1 weight percent to about 5.0 weight percent of the isopropyl alcohol. Preferably, the butylated hydroxytoluene is added to the reactant mixture at a concentration of about 1.0 weight percent of the isopropyl alcohol.

Preferably, the polymerization is carries out until the weight percent of the polyalphaolefin in the reactant mixture ranges from at least about 4 to about 12 weight percent polyalphaolefin. The weight percent of the polyalphaolefin in the reactant mixture more preferably ranges from at least about 5 to about 10 weight percent, and even more preferably ranges from at least about 7 to about 10 weight percent.

In another specific embodiment, the process is carried out in the absence of a hydrocarbon solvent until all available alpha olefin monomers have been exhausted, i.e., polymerized. Due to the absence of solvent, after the alpha olefin monomers have been polymerized, a polyalphaolefin block is formed. "Polyalphaolefin block" is herein defined as polyalphaolefin having a sufficiently high viscosity such that the polyalphaolefin is gel-like and may even retain its three-dimensional shape, e.g., a cylindrical block, at room temperature. The polyalphaolefin block is preferably a ductile or malleable mass which is resilient and tacky. The polyalphaolefins which form the polyalphaolefin block should be amorphous and substantially non-crystalline having an ultra-high molecular weight.

The polyalphaolefin block may then be used to reduce drag in a conduit by adding the polyalphaolefin block, or pieces of the polyalphaolefin block, to a conduit containing hydrocarbons. The polyalphaolefin block may also be further processed by any method known to those skilled in the art to be utilized to reduce drag in a conduit. For example, the polymer block may be frozen using liquid nitrogen and ground into smaller pieces which may then be directly combined with hydrocarbon in a conduit to reduce drag, or dissolved in a suspending material or dispersant and then combined with hydrocarbon in a conduit to reduce drag.

Figure 1:
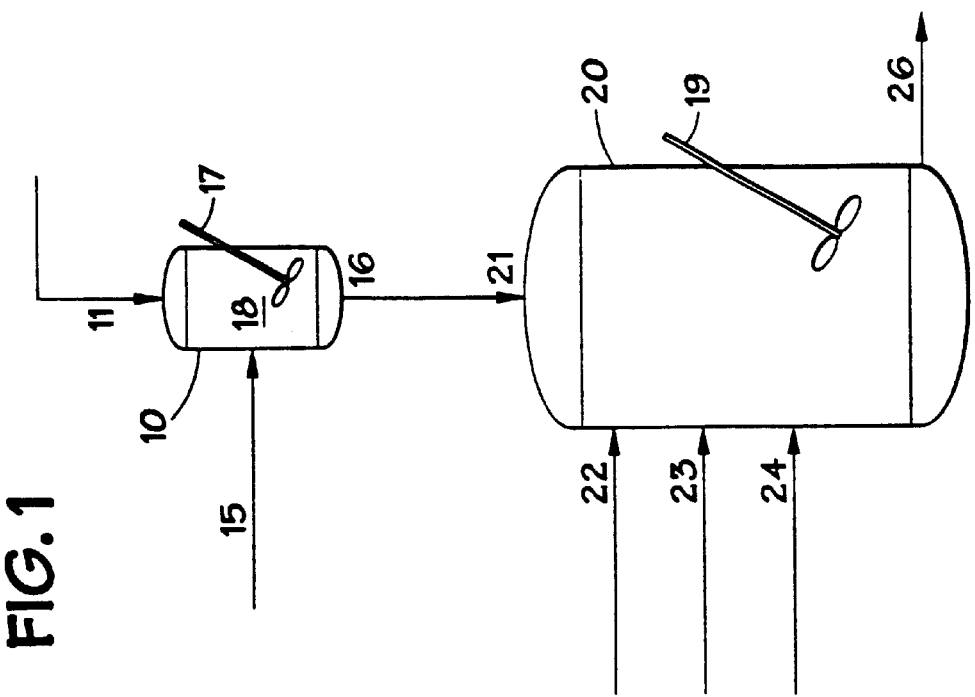
FIG. 1 is a flow diagram of a single-stage batch process.

The flow diagram of FIG. 1 illustrates a batch polymerization system used in one specific embodiment of the methods of the present invention. The system includes a catalyst preparation tank 10 and a batch reaction vessel 20. The catalyst preparation tank 10 includes a first inlet stream 11 that includes the transition metal catalyst and a second inlet stream 15 that includes a co-catalyst mixture. An appropriate mixing or agitation device 17 mixes the catalyst material with the co-catalyst mixture to form a catalyst system 18. An outlet 16 in communication with a first inlet 21 of the batch reaction vessel 20. Valves, pumps and other devices (not shown) can be used to control the flows of the various streams. The batch reaction vessel 20 has a second inlet for introduction of the alpha olefin monomer material in stream 22. The batch reaction vessel 20 also has a third inlet for the introduction of the hydrocarbon solvent in stream 23. In a specific embodiment of the invention, wherein a viscosity-reducing agent is utilized, a fourth inlet is included for introduction of a viscosity reducing agent that includes a substantially hydrophobic dispersant. Aromatic and/or aliphatic hydrocarbon solvent may be introduced together with the viscosity reducing agent through inlet 24 or, alternatively, may be introduced separately through inlet 23. Batch reaction vessel 20 can also include an appropriate mixing or agitation device 19. In one embodiment of the method, the catalyst system 18, prepared in the catalyst preparation tank 10, is introduced to the batch reaction vessel 20 through inlet 21 of the batch reaction vessel 20 and is mixed in desired proportions with the hydrocarbon solvent, viscosity reducing agent and alpha olefin material which are metered into the batch reaction vessel 20 through their respective inlets. Polymerization is initiated at appropriate temperatures and pressures. Alternatively, polymerization may be initiated at appropriate temperatures and pressures prior to the introduction of the viscosity reducing agent, the viscosity reducing agent thereafter being introduced during polymerization. Polymerization may be terminated naturally when all the monomer in the reactor is consumed, or, alternatively, by introducing a deactivator. The polyalphaolefin material formed by the process of polymerization may be withdrawn from the batch reaction tank 20 through inlet 26. Valves, pumps and other devices (not shown) may be interposed as necessary to remove the entire mixture, including formed polyalphaolefin, from the batch reaction polymerization vessel.

In accordance with another embodiment of this invention, shown in FIG. 2, a catalyst system 180 that includes a transition metal catalyst may be prepared in a catalyst preparation and storage vessel 100 by mixing the transition metal catalyst in stream 110, introduced through a first inlet 111, with co-catalyst mixture in stream 150 introduced through a second inlet 151 to form a catalyst system 180. The catalyst preparation and storage vessel may include a mixing or agitation device 170 as necessary. The catalyst preparation and storage vessel 100 has outlet 160 in communication with a first inlet 210 of a first reactor 200. The catalyst system 180 may be continuously metered from the catalyst preparation and storage vessel 100 through outlet 160 in communication with first inlet 210 into the first reactor 200 whereby the catalyst system 180 is mixed in desired proportions with alpha olefin monomers in stream 220 introduced through second inlet 221 and hydrocarbon solvent stream 235, introduced through a third inlet 236, which are continuously metered from other sources not shown. Polymerization is initiated in the first reactor 200 at appropriate temperatures and pressures. First reactor 200 includes an appropriate mixing or agitation device 270 and an outlet 250 for continuous removal of polyalphaolefin and the other materials in the reactor 200. A viscosity reducing agent in stream 240, which includes a substantially hydrophobic dispersant, may also be metered from a separate source into the first reactor 200 through a fourth inlet 241 prior to commencing the polymerization reaction. Additionally, or alternatively, the viscosity reducing agent may be metered into the first reactor 200 through the fourth inlet 241 during polymerization. Additional reactors may also be provided in which polymerization continues and from which non-crystalline, ultra-high molecular weight polyalphaolefin product may be recovered.

In another specific embodiment, referring to FIG. 3, a second reactor 300 is provided in which the materials of the first reactor 200 (also shown in FIG. 2), including catalyst system, unreacted alpha olefin, oligomers and polyalphaolefin, may be pumped continuously from outlet stream 250 of the first reactor by pump 260 into the second reactor 300 through inlet stream 310, where the molecular weight of the polyalphaolefin drag reducing agent polymer is further increased. Additionally, a viscosity reducing agent in stream 240 may also be metered into the second reactor 300 through fourth inlet 241. Second reactor 300 includes an appropriate mixing or agitation device 370 and outlet 380 for removal of the DRA product which includes polyalphaolefin and the other remaining materials in second reactor 300. Removal of the polyalphaolefin and other remaining materials in reactor 300 may be accomplished by pump 390. Valves, pumps and other devices (not shown) may be interposed as necessary. As another feature of this invention, fresh reactants may be added to the first reactor 200 as material is being pumped from the first reactor 200 to the second reactor 300. The reaction may be terminated by introducing a deactivator (not shown) or, alternatively, the reaction may terminate naturally when all the monomer in the reactors are consumed. Preferably, excess alpha olefin monomers are present during polymerization and deactivator is added to the reactant mixture to halt polymerization once the non-crystalline, ultra-high molecular weight polyalphaolefin is formed. As an additional option and additional feature of this specific embodiment of the invention, the reaction may be continued by forwarding the formed polyalphaolefin and other remaining materials to a pressurized storage vessel (not shown) where the molecular weight of the formed polyalphaolefin may yet be further increased. The polyalphaolefin drag reducing agent may be introduced into a conduit to reduce frictional energy losses of the material flowing through the conduit.

Examples of suitable polymerization reactions are shown in U.S. Pat. No. 6,015,779, which are hereby incorporated by reference.

Comparative examples of drag reducing agents formed from isomerized alpha olefins and drag reducing agents formed from unisomerized alpha olefin monomers were prepared in accordance with the discussion above. Results of the comparison are shown below in TABLE II. The abbreviation "PAO" means polyalphaolefin. As shown in TABLE II, the percent drag reduction of drag reducing agents formed from isomerized alpha olefin monomers, i.e., alpha olefin monomers that have been isomerized as discussed above, was greater than the percent drag reduction of drag reducing agents formed from alpha olefin monomers that had not been isomerized.

TABLE II

| Alpha Olefin Monomers | Isomerized (Yes or No) | % Drag Reduction (at 1.0 ppm PAO in hexane) | % Flow Increase (at 1.0 ppm PAO in hexane) |
|---|---|---|---|
| $C_6$–$C_{12}$ | Yes | 40.1 | 31.0 |
| $C_6$–$C_{12}$ | No | 23.3 | 15.0 |
| $C_8$–$C_{14}$ | Yes | 36.3 | 26.7 |
| $C_8$–$C_{14}$ | No | 17.6 | 10.7 |
| $C_{10}$ | Yes | 38.8 | 29.5 |
| $C_{10}$ | No | 20.3 | 12.7 |

As mentioned above, it is contemplated that any isomerization process that results in substantially all of the branched olefins being isomerized into straight olefin may be used connection with any polymerization process for forming drag reducing agents. From these examples, it can be seen the embodiments of the present invention provide superior properties when compared to other drag reducing agents. As mentioned above, while the examples reflect specific embodiments of the invention, the following claims, including their equivalents, will define the scope of the protected invention.

What is claimed is:

1. A process for forming an ultra-high molecular weight polyolefin drag reducing agents by polymerizing at least one olefin monomer in the presence of at least one catalyst, wherein the improvement comprises:
   isomerizing the at least one olefin monomer prior to polymerizing the at least one olefin monomer in the presence of at least one catalyst.

2. The process of claim 1, wherein the at least one olefin monomer includes at least one alpha olefin monomer.

3. The process of claim 2, wherein the at least one alpha olefin monomer includes at least one of 1-hexene, 1-octene, 1-decene, 1-dodecene, or mixtures thereof.

4. The process of claim 2, wherein the at least one alpha olefin monomer includes a combination of 1-hexene and 1-dodecene alpha olefin monomers or a combination of 1-octene and 1-tetradadecene alpha olefin monomers.

5. A process for forming a drag reducing agent comprising a substantially non-crystalline, ultra-high molecular weight polyolefin, the process comprising:
   isomerizing olefin monomers to form isomerized olefin monomers, wherein the isomerized olefin monomers are substantially free of branched olefin monomers;
   contacting isomerized olefin monomers with a catalyst system in a reactant mixture, wherein the catalyst system includes at least one catalyst and at least one co-catalyst; and
   polymerizing the isomerized olefin monomers at a temperature at about or less than 25° C., wherein during the polymerization, at least a portion of the isomerized olefin monomers polymerize in the reactant mixture to provide a substantially non-crystalline, ultra-high molecular weight polyolefin.

6. The process of claim 5, wherein the olefin monomers are alpha olefin monomers.

7. The process of claim 6, wherein the alpha olefin monomer includes at least one of 1-hexene, 1-octene, 1-decene, 1-dodecene, or mixtures thereof.

8. The process of claim 6, wherein the alpha olefin monomer includes a combination of 1-hexene and 1-dodecene alpha olefin monomers or a combination of 1-octene and 1-tetradadecene alpha olefin monomers.

9. The process of claim 5, wherein the olefin monomers are polymerized by bulk polymerization.

10. The process of claim 5, wherein the polymerization of the olefin monomers continues such that polyolefin is present in the reactant mixture at a concentration of at least about 4 weight percent based upon the weight of the reactant mixture, and the polyolefin includes an inherent viscosity afar least about 10 deciliters per gram.

11. The process of claim 5, wherein the at least one co-catalyst includes an alkylaluminoxane.

12. The process of claim 11, wherein the alkylaluminoxane is selected from the group consisting of methylaluminoxane and isobutylaluminoxane.

13. The process of claim 5, wherein the at least one catalyst includes a transition metal catalyst.

14. The process of claim 13, wherein the transition metal catalyst is a non-metallocene transition metal catalyst.

15. The process of claim 14, wherein the non-metallocene transition metal catalyst includes titanium trichloride.

16. The process of claim 5, wherein the at least one co-catalyst includes a halohydrocarbon.

17. The process of claim 16, wherein the halohydrocarbon is a chloride containing halohydrocarbon.

18. The process of claim 17, wherein the chloride containing halohydrocarbon is ethylene dichloride.

19. The process of claim 5, wherein the isomerized olefin monomers are polymerized by bulk polymerization.

* * * * *